United States Patent [19]
Gramling et al.

[11] Patent Number: 5,489,982
[45] Date of Patent: Feb. 6, 1996

[54] METHOD FOR DETERMINING A VISUAL RANGE

[75] Inventors: Hubert Gramling, Ebersbach; Horst Hahn, Renningen; Wolfgang Lauer, Heilbronn, all of Germany

[73] Assignee: Daimler-Benz AG, Stuttgart, Germany

[21] Appl. No.: 180,301

[22] Filed: Jan. 12, 1994

[30] Foreign Application Priority Data

Jan. 12, 1993 [DE] Germany .......................... 43 01 228.0

[51] Int. Cl.$^6$ ...................................... G01C 3/08
[52] U.S. Cl. ................... 356/5.05; 356/4.07; 356/5.06
[58] Field of Search ................................. 356/4.07–5.01, 356/5.05–5.07, 342

[56] References Cited

U.S. PATENT DOCUMENTS

| | | |
|---|---|---|
| 3,519,354 | 7/1970 | Brown, Jr. et al. . |
| 3,782,824 | 1/1974 | Stoliar et al. . |
| 4,502,782 | 3/1985 | Werner et al. . |
| 4,605,302 | 8/1986 | Lofgren et al. . |
| 4,699,507 | 10/1987 | Etoh . |
| 4,722,599 | 2/1988 | Fruengel et al. . |

FOREIGN PATENT DOCUMENTS

| | | |
|---|---|---|
| 3640449 | 6/1988 | Germany . |
| 4005919 | 4/1991 | Germany . |
| 2224175 | 4/1990 | United Kingdom . |
| WO88/08546 | 11/1988 | WIPO . |

OTHER PUBLICATIONS

*Applied Optics*, vol. 24, No. 21, pp. 3523–3525 entitled "Visibility Related To Backscatter at 1.06 μm" by T. L. Barber & D. R. Larson

*Primary Examiner*—Stephen C. Buczinski
*Attorney, Agent, or Firm*—Evenson, McKeown, Edwards & Lenahan

[57] ABSTRACT

A method for determining the visual range improves the visual range measurement adopted as a basis, to the end that the measurement of the visual range can take place using one emitter and using one receiver, which are disposed to be stationary. The method permits the determination of the visual range, even though an obstacle is situated within the field of view. A comparison of a measured backscatter signal with a specimen curve permits the determination of the visual range from the intensity curve obtained, without any need, for this purpose, of further information such as, for example, the direction from which the backscatter signal comes.

8 Claims, 3 Drawing Sheets

METHOD FOR DETERMINING A VISUAL RANGE

BACKGROUND AND SUMMARY OF THE INVENTION

The invention relates to a method for determining a visual range from the backscatter signal of a light pulse emitted by a light source. In this method, a small part of the emitted light signal is coupled-in directly into a receiver for the normalization of the backscatter signal with the intensity of the emitted light pulse. Furthermore, in the receiver, the intensity of the backscatter signal is measured as a function of the transit time which has elapsed since the emission of the light pulse. A conclusion is drawn from the transit time of the backscatter signal as to the distance from a backscatterer.

Such a method is disclosed, by way of example, in German Patent document DE 4,005,919 C1. In the known German Patent document, it is proposed, for the measurement of visual range, to arrange in the front region of a vehicle, an emitter which is pivotable about a horizontal axis and which at regular time intervals emits light pulses directed onto the roadway at differing angles of inclination. The reflected, backscattered light pulses are received in a receiver arrangement. In this case, a plurality of receivers are disposed at respectively different angles of inclination in relation to the horizontal.

The signals emitted from the emitter pass onto the surface of the road at a distance which is essentially dependent upon the angle of inclination. The signals are reflected by the road surface and the reflected signal is measured in the appropriately inclined receiver.

A visual range measurement requires a plurality of individual measurements which in each instance only establishes whether it is or is not possible to see to a specified distance. Only all measurements together permit a statement to be made concerning the actual visual range. Furthermore, either an emitter must be disposed to be pivotable and controlled, which emitter emits the signal in a precisely predetermined direction, or it is necessary to dispose a plurality of individually driven, mutually inclined emitters. In any event, it is necessary to dispose a large number of receivers on the vehicle, to permit a determination to be made of the angle at which the reflected signals are incident, in relation to the horizontal.

In this manner, where an obstacle is situated within the visual range, it is not possible to determine the visual range but at best only the distance of the obstacle from the vehicle. It is to be seen as a further disadvantage that this distance measurement gives useful measurement values only on straight portions of a path of travel.

The object of the invention is to improve the visual range measurement adopted as a basis according to the relevant category to the end that the measurement of the visual range can take place using one emitter and using one receiver. The emitter and receiver are stationarily disposed. The intention is also to permit the determination of the visual range, even when an obstacle is situated within the field of view.

Adopting as a basis the visual range measurement according to the relevant category, this object is achieved according to the invention by a method for determining the visual range from the backscatter signal of a light pulse emitted by a light source. In this method, a small part of the emitted light signal is coupled-in directly into a receiver for the normalization of the backscatter signal with the intensity of the emitted light pulse. Furthermore, in the receiver, the intensity of the backscatter signal is measured as a function of the transit time which has elapsed since the emission of the light pulse. A conclusion is drawn from the transit time of the backscatter signal as to the distance from a backscatterer. A specimen curve, dependent upon at least two parameters of the intensity progression is adapted to the measured backscatter signal by determination of the parameters. At least one of the parameters is employed as a measure of the visual range.

The comparison with a specimen curve permits the determination of the visual range from the intensity curve obtained, without any need, for this purpose, of further information such as for example the direction from which the backscatter signal comes. It thus also becomes possible to determine a value for the visual range from each emitted pulse, so that it is also no longer necessary to evaluate a plurality of measurement results in order to obtain an indication of the visual range. As a result of this, it is also possible to attain a higher measurement frequency, since the duration of an emitted pulse does not need to be any greater than is the case when using the known arrangement. The method is suitable both for the stationary measurement of the visual range and also for use in a vehicle.

By a dual evaluation of the backscatter signal obtained from a measurement, it is moreover possible in an embodiment of the invention to also determine the visual range in circumstances in which an obstacle is situated within the field of view. After a first evaluation, in which the parameters are first determined, the measured intensity distribution is investigated for a limited region of great increase of the measured intensity from the specimen curve. In the event that such a region is present, this signal is interpreted as backscatter by an obstacle. The distance of the obstacle from the vehicle is then obtained from the transit time of the increased signal. To determine the visual range, a second computation of the parameters is carried out. In this case, the region of the signal increase is left out of consideration in the computation of the parameters.

Other objects, advantages and novel features of the present invention will become apparent from the following detailed description of the invention when considered in conjunction with the accompanying drawings.

DETAILED DESCRIPTION OF THE DRAWINGS

Figure 1:
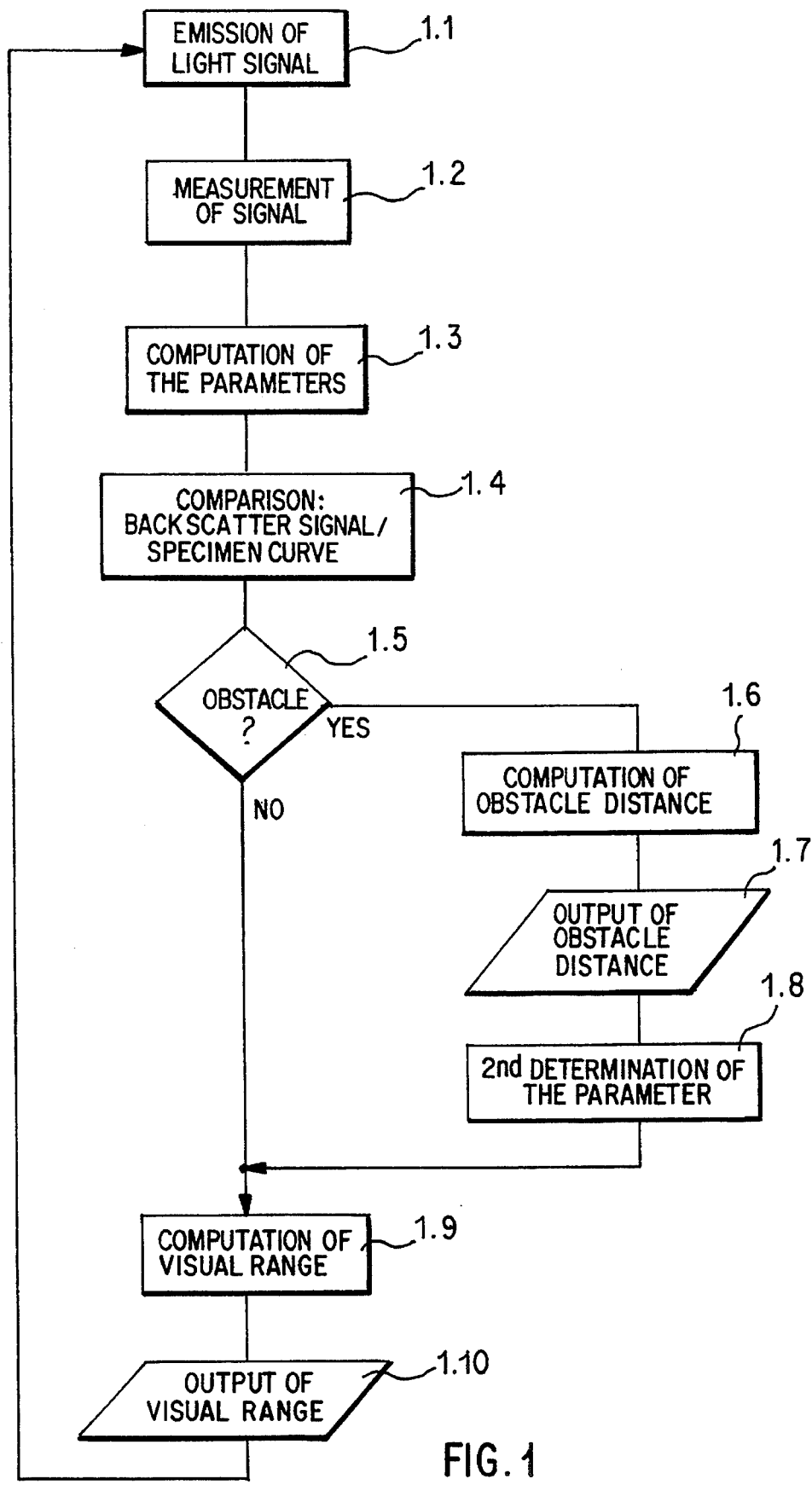
FIG. 1 is a flow diagram of the method of measurement according to the present invention.

FIG. 1 shows, in a flow diagram format, the sequence of the individual steps of a method according to the present invention. In step 1.1, a light pulse 19 (FIG. 3) is emitted by the emitter 21. This pulse is preferably the light pulse 19 of a pulsing laser in the infrared spectral range. A certain small part of the light pulse 19 is introduced directly into the receiver 22. The other light passing into the receiver 22 is backscattered light. The signal obtained during the measurement 1.2 is measured as a discrete time sequence of the measured intensity I of the backscatter signal 10. Subsequently, in step 1.3, the computation of the parameters a,b takes place in accordance with the method of least squares. In the method step 1.4, the backscatter signal 10 is compared with the specimen curve 11 obtained in step 1.3. In the event that in the region BII (FIG. 2) of the specimen curve 11 there is a considerably higher backscatter signal 10 than the specimen curve 11, this is interpreted as an obstacle 29 located within the visual range. If an obstacle 29 is present, then step 1.5 branches to the steps 1.6 to 1.8. Otherwise, a jump takes place to the method step 1.9.

In the step 1.6, the computation of the distance d from the obstacle 29 takes place from the transit time $t_H$ of the backscatter signal 10. In this case, it has to be taken into consideration that the measured transit time $t_H$ is the time required for the outward and return path of the light pulse. The computed distance d is indicated in step 1.7. Subsequently, a renewed computation 1.8 of the parameters a,b takes place. In this case, the signal obtained in the region of the increased backscatter signal 15 is not taken into consideration. As a result of this, an improved value of the visual range s is determined. The computation of the visual range s takes place from a linear relation between the visual range s and the reciprocal of the parameter a. The computed visual range 8 is indicated in step 1.10, and the next measurement is carried out.

Where an obstacle 29 is detected within the range of vision, in a further embodiment of the invention the relative velocity of the obstacle 29 in relation to the vehicle can be determined in that the measured distance from an obstacle is monitored over a plurality of measurements and the relative velocity is computed from its change and indicated.

Figure 2:
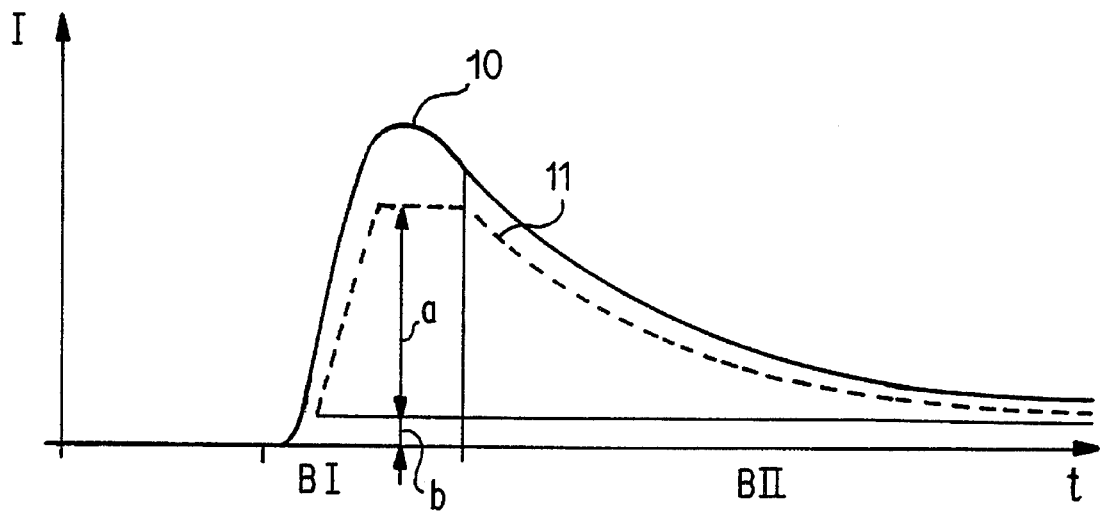
FIG. 2 is an ideal representation of the backscatter signal and a representation of the specimen curve.

FIG. 2 shows a representation of the ideal, error and disturbance free backscatter signal 10 in fog. During a short first period of time after the emission of the light pulse 15, no signal is yet received in the receiver 22. After this, a high light intensity I due to the direct return passage of a small part of the light pulse 19 emitted by the emitter 21 is caused in the receiver 22. However, this signal is only of the duration of the emitted light pulse 19. There is superimposed thereon the light which is backscattered in the immediate vicinity of the emitter 21 and which likewise exhibits a relatively high light intensity. The signal progression shown in the region BI is obtained. The intensity I measured from the backscattered light in the receiver 22 decreases as a function of the distance of the condition causing the backscatter from the emitter 21 or receiver 22. As long as the backscattering does not take place in a directional manner, i.e. does not take place in a manner controlled by any reflectors whatsoever, it is proportional to the reciprocal of the square of the distance between the condition causing the backscatter and the receiver. This determines the form of the curve of the intensity in the region BII. However, it has to be taken into consideration that the intensity of the light pulse incident on the condition causing the backscatter also decreases with the distance d between receiver 22 and the condition causing the backscatter. However, this can be disregarded to a first approximation. This gives as a possible specimen curve 11 for the region BII the function $M(t) = a/t^2 + b$. In the region BI, the specimen curve 11 then exhibits a plateau of height a+b, to which the function rises, for example linearly. The specimen curve 11 can however also exhibit other forms. By means of a factor which is possibly also dependent upon the distance d of the transit time t, it is possible to take into account the light pulse intensity which decreases exponentially as a result of scattering. However, it is also possible to introduce terms of higher power of the distance as a series expansion. The specimen curve 11 in the region BII would then have, by way of example, the form $M(t) = a/t^2 + b/t^3 + c$. A more complicated expression for the specimen curve 11 does however lead to more computing effort in the computation of the parameters. Thus, the simple approximation shown here exhibits the advantage that the computations can be carried out in a simpler manner, that is to say faster and using simpler processors.

The specimen curve is represented in the figures as a function of the transit time t, since the transit time t is the measurable quantity. The distance d is computed from the transit time t by means of the linear relation $2*d = v*t$; in this expression, v is the velocity of light. A value of the visual range s can be determined in a simple manner from the relation $s = R/a$. This takes into account the fact that,the intensity of the backscattered light is proportional to the density of the backscatterer, i.e. for example to the fine water droplets which form the fog. The factor a is proportional to the intensity of the backscattered light. On the other hand, the visual range s is poorer with the higher the density of the condition causing the backscatter. Accordingly, the reverse proportionality can be assumed in the relation between visual range s and parameter a. In this case also, it is possible to achieve a higher resolution or accuracy of measurement by using more complicated computation models which better reproduce the reality. With the simple relations represented here, an adequate accuracy of measurement is however achieved. The parameter b of the simple presented parametric statement corresponds in these circumstances to an offset which cannot be suppressed in the course of the measurement. It comes, for example, from the infrared spectrum of the headlights and of daylight.

Since simply constructed lasers which are employed as the emitter 21 are not stable, especially under conditions of operation such as those prevailing in motor vehicles, but rather fluctuate in the intensity of the emitted light pulse 19, this intensity must be measured. As a result of the fact that a given part of the signal 19 is introduced into the receiver, a conclusion can be drawn as to the intensity of the light pulse 19 from the maximum intensity of the backscatter signal 10. By means of an appropriate normalization to a standard intensity of the light pulse, the computation error of the parameters a,b which results from the signal fluctuations can be avoided.

Figure 3:
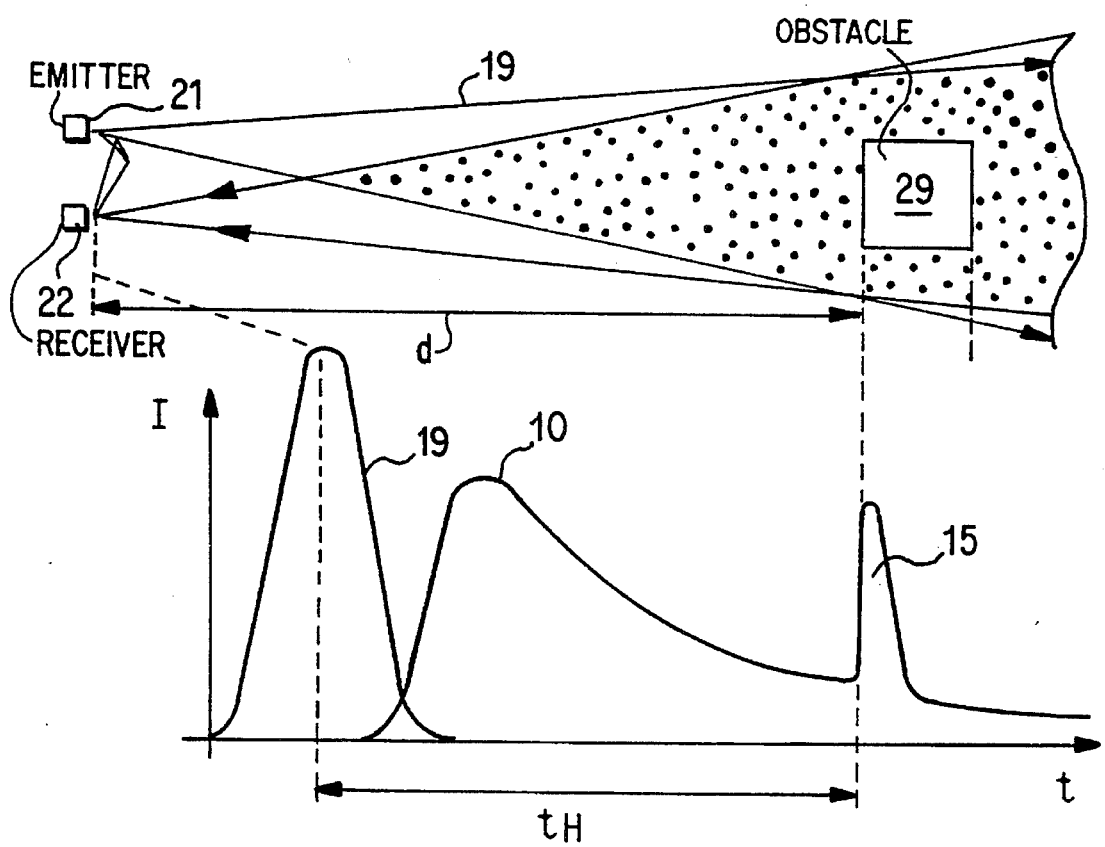
FIG. 3 is a diagrammatic representation of a measurement, as well as of the backscatter signal obtained in this case.

FIG. 3 shows a diagrammatic representation of a measurement and of the backscatter signal obtained in the course of the measurement; in this case, an obstacle 29 is situated within the range of measurement. The emitter 21 emits the light pulse 19. A small part of the light pulse is introduced directly into the receiver 22. The remainder of the light measured in the receiver passes thereto by backscattering. Apart from the increase 15, the expected progression of the backscatter signal 10 is obtained. The increase 15 accordingly arises from the fact that the light pulse is reflected or scattered at the obstacle 29. A higher proportion of the incident light pulse 19 is directed back into the receiver 22. The distance d of the obstacle 29 from the vehicle is computed from the transit time $t_H$ of the light reflected by the obstacle. The following relation is applicable: $d = v*t_H/2$; in this case, v stands for the velocity of light. The factor 2 takes into account the dual passage of the distance d by the light pulse 19. The computed distance d of the obstacle can be indicated to the driver. From the change of the distance of the obstacle from the vehicle between a plurality of successive measurements, it is possible to draw a conclusion as to the relative velocity between the vehicle and the obstacle 29. This measure is of interest especially in the case of obstacles which are situated within the region of the visual range 8 ahead of the vehicle.

Figure 4A:
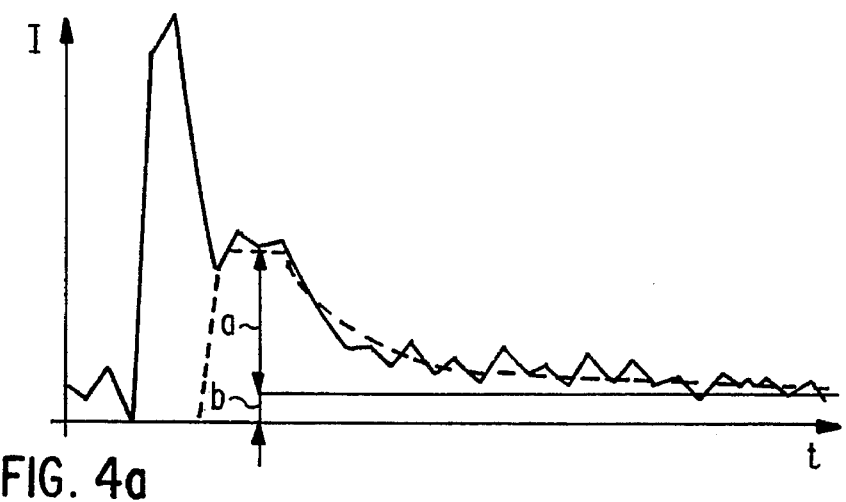
FIGS. 4a and 4b illustrate the progression of the backscatter signal and the specimen curve.
Figure 4B:
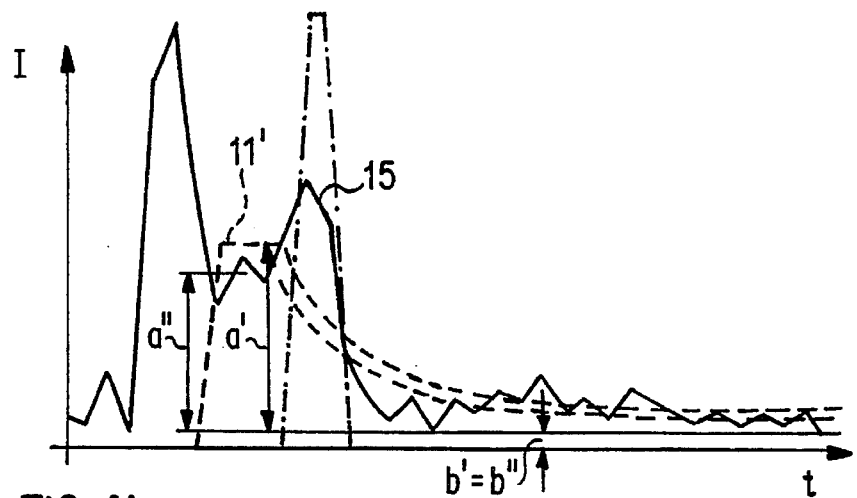

FIGS. 4a and 4b show the intensity curves, obtained in the course of measurements, of the backscatter signal in the receiver 22, and the approximated specimen curves 11. The measured backscatter signal is represented as a solid line, the computed specimen curve 11, 11' and 11" as broken lines, and the obstacle as a dash-dotted line.

The simple specimen curve $M(t)=a/t^3+b$ was used. It becomes clear that the parameter a is the parameter which is relevant for the purposes of the adaptation to the backscattering and thus of the determination of the visual range. FIG. 4b shows to what extent the two stage computation of the parameters influences the accuracy of measurement when an obstacle is detected within the region BII of the measured signal. As a result of the increase 15, in the case of the first parameter computation, the value a' of the parameter a is determined. For the second computation of the parameters, that region of the measured values which corresponds to the obstacle shown in dash-dotted lines and magnified was not taken into consideration. This gives a second value a" of the parameter a, which represents a more precise measurement of the visual range than the first computation. The second value a" is in principle smaller than the value a', and the visual range s resulting therefrom is greater. It corresponds to the given conditions of vision, since the signal generated by the obstacle has been eliminated in the computation process.

However, with this method it is not possible to detect an obstacle located within the region 1 if the obstacle is superposed by the direct backscatter signal. The parameter a is still only correctly determined if the obstacle allows a large part of the laser pulse to pass. However, this is not a defect of the acquisition of the obstacles or the visual range, since this affects only obstacles which are situated a few meters ahead of the emitter, and thus normally have already been detected by the driver. Accordingly, this embodiment of the visual range measurement in this form cannot be used as a parking aid. In principle, it is possible also to detect, by a suppression of the direct coupling-in of a part of the light pulse 19 into the receiver 22, obstacles which are situated very close to the vehicle and to indicate their distance. A reasonable measurement of the visual range is then however only possible if the intensity of the light pulse is measured, for example, by a second receiver.

Furthermore, it should be noted that the value of the parameter b which can be associated with the ambient light is hardly at all influenced by the dual computation in the case of an obstacle.

Figure 5:
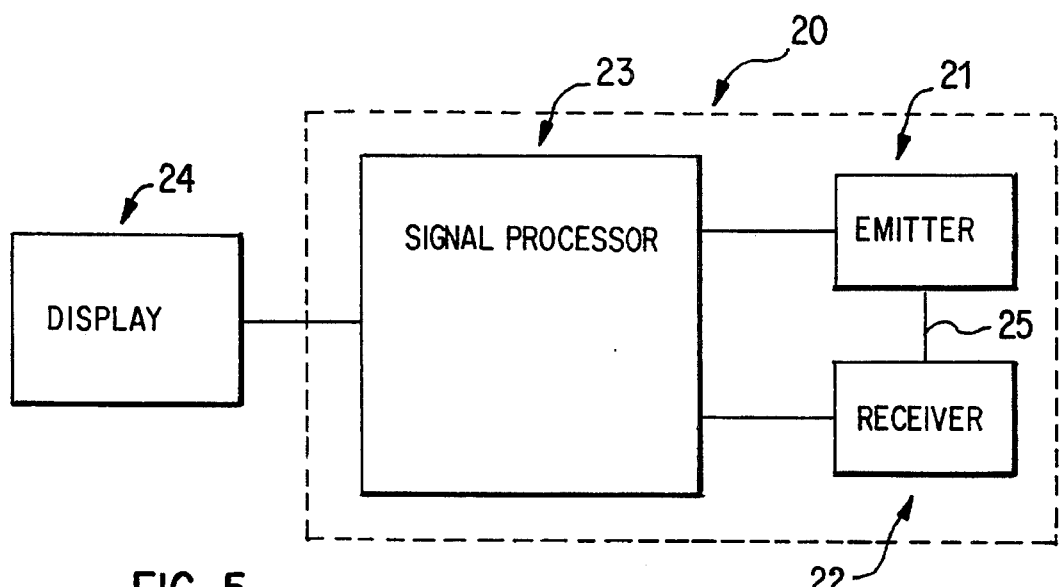
FIG. 5 is a schematic block diagram representation of a visual range measuring system which is suitable for carrying out the method according to the present invention.

FIG. 5 shows, in a diagrammatic representation, a visual range measuring system 20 which is suitable for carrying out the method. The display 24 communicates to the driver the measured visual range and possibly the distance from the obstacle. The signal processing 23 carries out the computations and controls emitter 21 and receiver 22. The feedback 25 conducts a known part of the light pulse 19 directly into the receiver 22. The intensity of a light pulse 19 is at approximately an output power of 20 watts with a pulse duration of 6 ns. In this case, it has to be kept in mind that the measurement result is improved with an increasing intensity of the light pulse 19. However, it is necessary to avoid endangering third parties by the emitted light pulse 19.

Thus, its maximum intensity is given an upper limit by the appropriate radiation directives. The intensity of the backscatter signal decreases with the distance and, in the case of small backscatterers, at which the incident light experiences a uniform diffusion, is in ranges of a few nW. However, such small intensities are measurable.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for determining a visual range from a backscatter signal of a light pulse emitted by a light source, the method comprising the steps of:

directly coupling-in into a receiver a small part of the emitted light pulse for normalization of the backscatter signal with an intensity of the light pulse;

measuring in the receiver the intensity of the backscatter signal as a function of a transit time elapsed since the light pulse was emitted;

concluding from the transit time of the backscatter signal a distance from a backscatterer;

adapting a specimen curve of the intensity progression, dependent upon at least two parameters, to the measured backscatter signal by determining the at least two parameters; and employing at least one of said parameters as a measure of the visual range.

2. A method according to claim 1, wherein the specimen curve exhibits the form $M(t)=a* F(t)+b$, where a,b are the parameters to be determined and F(t) is a parameter-free basic function.

3. A method according to claim 2, wherein the basic function comprises two regions, the first region being a step function onto a plateau and the second region being a decaying function.

4. A method according to claim 2, wherein the visual range is determined by a linear relation from the reciprocal of the parameter a.

5. A method according to claim 1, wherein the computation of the parameters takes place in accordance with the method of least squares.

6. A method according to claim 1, wherein a great increase of the intensity in one region of the backscatter signal in relation to the backscatter signal expected in relation to the approximated specimen curve is interpreted as an obstacle, and in that the distance from the obstacle is computed from the transit time of this increased backscatter signal.

7. A method according to claim 6, wherein in the event of an increase of the backscatter signal in relation to the approximated specimen curve occurring in the second region, a renewed computation of the parameters takes place, in which case the region of the increased intensity is not utilized for the computation of the parameters, and in that the new computed parameters are utilized for the computation of the visual range.

8. A method according to claim 3, wherein in the event of an increase of the backscatter signal in relation to the approximated specimen curve occurring in the second region, a renewed computation of the parameters takes place, in which case the region of the increased intensity is not utilized for the computation of the parameters, and in that the new computed parameters are utilized for the computation of the visual range.

* * * * *